(12) United States Patent
Corre et al.

(10) Patent No.: US 10,173,954 B2
(45) Date of Patent: Jan. 8, 2019

(54) PROCESS FOR HYDROXYLATION OF AROMATIC COMPOUNDS, HYDROXYLATION CATALYST AND PROCESS FOR PREPARING SAME

(71) Applicants: Rhodia Operations, Paris (FR); CENTRE NATIONAL DE LA RECHERCHE SCIENTIFIQUE (C.N.R.S.), Paris (FR)

(72) Inventors: Thibaut Corre, Soucieu-en-Jarrest (FR); Belen Albela, Lyons (FR); Laurent Bonneviot, Lyons (FR); Laurent Garel, Lyons (FR)

(73) Assignees: Rhodia Operations, Paris (FR); CENTRE NATIONAL DE LA RECHERCHE SCIENTIFIQUE—C.N.R.S., Paris (FR)

( * ) Notice: Subject to any disclaimer, the term of this patent is extended or adjusted under 35 U.S.C. 154(b) by 0 days.

(21) Appl. No.: 15/598,400

(22) Filed: May 18, 2017

(65) Prior Publication Data
US 2017/0253547 A1 Sep. 7, 2017

Related U.S. Application Data

(62) Division of application No. 14/378,656, filed as application No. PCT/EP2013/053054 on Feb. 15, 2013, now Pat. No. 9,682,909.

(30) Foreign Application Priority Data

Feb. 17, 2012 (FR) ...................................... 12 51496

(51) Int. Cl.
| | | |
|---|---|---|
| *C01B 39/06* | (2006.01) | |
| *C01B 39/36* | (2006.01) | |
| *C07C 37/60* | (2006.01) | |
| *B01J 29/89* | (2006.01) | |
| *B01J 35/02* | (2006.01) | |
| *C07C 37/58* | (2006.01) | |
| *C01B 37/00* | (2006.01) | |
| *B01J 35/00* | (2006.01) | |
| *B01J 37/08* | (2006.01) | |

(52) U.S. Cl.
CPC ............... *C07C 37/60* (2013.01); *B01J 29/89* (2013.01); *B01J 35/006* (2013.01); *B01J 35/0013* (2013.01); *B01J 35/023* (2013.01); *B01J 37/08* (2013.01); *C01B 37/005* (2013.01); *C01B 39/065* (2013.01); *C01B 39/36* (2013.01); *C07C 37/58* (2013.01); *C01P 2004/61* (2013.01); *C01P 2006/12* (2013.01); *C01P 2006/16* (2013.01)

(58) Field of Classification Search
CPC ..... C01B 37/005; C01B 39/065; C01B 39/36; C01P 2004/61; C01P 2006/12; C01P 2006/16; B01J 29/89; B01J 35/023; B01J 35/0013; B01J 35/116; B01J 35/08
See application file for complete search history.

(56) References Cited

U.S. PATENT DOCUMENTS

| | | | | |
|---|---|---|---|---|
| 4,410,501 A | * | 10/1983 | Taramasso | ................ B01J 29/89 423/705 |
| 7,211,239 B2 | * | 5/2007 | Muller | .................. C01B 37/005 423/702 |

* cited by examiner

*Primary Examiner* — David M Brunsman
(74) *Attorney, Agent, or Firm* — Osha Liang LLP

(57) ABSTRACT

The present invention relates to a process for hydroxylation of a compound of formula (I) by reacting the compound of formula (I) with an oxidizing agent, in the presence of a titanium silicalite zeolite prepared by crystallization preceded by a maturing step. The present invention also relates to a titanium silicalite zeolite and to the process for preparing same.

7 Claims, 4 Drawing Sheets

PROCESS FOR HYDROXYLATION OF AROMATIC COMPOUNDS, HYDROXYLATION CATALYST AND PROCESS FOR PREPARING SAME

CROSS-REFERENCE TO RELATED APPLICATIONS

The present application is a divisional filed pursuant to 35U.S.C. § 121 of U.S. patent application Ser. No. 14/378.656, filed on Aug. 14. 2014, now U.S. Pat. No. 9,682,909 which is a U.S. national stage entry under 35U.S.C. § 371 of International Application No. PCT/EP2013/053054 filed Feb. 15. 2013, which claims priority to FR Application No. 12.51496 filed on Feb. 17. 2012, the whole content of these applications being herein incorporated by reference for all purposes.

The hydroxylation of aromatic compounds, such as phenols, in the presence of an oxidizing agent, especially aqueous hydrogen peroxide solution, and of a catalyst leads to the formation of hydroxylated aromatic compounds, such as hydroquinone (HQ) and pyrocatechol (PC) for phenol, but also to the formation of side products, especially tars. To limit the formation of these tars, the conversion of the starting aromatic compound should be limited, and is, for example, in the case of phenol, from 5% to 30%.

More specifically, the demand for hydroquinone is relatively high, especially in the field of polymerization inhibitors. One way of satisfying this increasing demand for hydroquinone would be to orient the hydroxylation reaction of phenol toward the formation of hydroquinone.

The prior art, especially FR 2 071 464 discloses the use of a homogeneous catalyst of optionally modified strong acid type, for the hydroxylation of phenol. The use of this hydroxylation reaction of phenol in the presence of a homogeneous strong acid catalyst leads to the formation of hydroquinone and pyrocatechol in a PC/HQ mole ratio, depending on the acid used, of greater than or equal to 1.5. In general, the use of a homogeneous catalyst leads to the formation of hydroquinone and pyrocatechol in a PC/HQ mole ratio of greater than or equal to 1.

It is also known from the prior art, especially from FR 2 523 575, to use a zeolite of titano-silicalite type of structure MFI or MEL, especially TS-1 or TS-2, respectively, a heterogeneous catalyst, for the hydroxylation of phenol. It is thus possible to obtain hydroquinone and pyrocatechol with a PC/HQ mole ratio of less than 1.3, especially between 0.4 and 1.3, depending on the catalyst or the solvent used in the phenol hydroxylation reaction.

It is, however, worthwhile providing a process for obtaining the lowest possible PC/HQ mole ratio in order to promote the formation of hydroquinone while at the same time maintaining the highest possible yield in an environmentally friendly solvent such as water.

TS-1 and TS-2 are zeolites characterized by the presence of titanium atoms in replacement for silicon atoms in the structure. These zeolites have, respectively, a structure MFI or MEL and are generally obtained by mixing a source of silicon, a source of titanium, a structuring agent and a mineralizing agent, the mixture obtained then being crystallized for 1 to 10 days at a temperature typically close to 175° C. and finally calcined for 3 to 12 hours, at a temperature typically close to 550° C. Processes for preparing TS-1 are especially described in U.S. Pat. No. 4,410,501 or EP 0 311 983.

TS-1 and TS-2 have advantageous catalytic properties and are thus used in many reactions such as the hydroxylation of phenol, the ammoximation of cyclohexanone or the epoxidation of alkenes.

Many studies have been conducted aimed at improving the catalytic performance of titano-silicalite zeolites. These studies have related especially to the crystallization time, the source of silicon, the source of structuring agent, the TPAOH/Si mole ratio, the $H_2O$/Si mole ratio or the Ti/(Ti+Si) mole ratio (Van Der Pol et al., Appl. Catal. A General, 1992 92 93-111).

An optimized process should be found for preparing titanium silicalites such as TS-1 or TS-2, making it possible to improve their catalytic properties, especially in the context of the hydroxylation reaction of aromatic compounds, and in particular of phenol.

One object of the present invention is to provide an improved process for the hydroxylation of aromatic compounds, and in particular of phenol, anisole and para-t-butylphenol.

Another object of the present invention is to provide a process for the hydroxylation of phenol which allows the preparation of hydroquinone and pyrocatechol with a PC/HQ mole ratio of less than 1.4, preferably less than 1.2, more preferably less than 1, preferably strictly less than 0.8 and preferably strictly less than 0.7.

Another object of the present invention is to provide a titano-silicalite zeolite that is suitable for use in this process for the hydroxylation of aromatic compounds.

Other objects will become apparent on reading the description of the invention that follows.

The present invention relates to a process for the hydroxylation of a compound of formula (I):

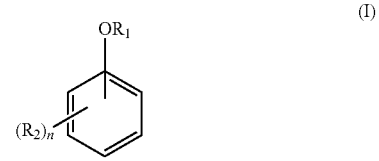

in said formula:
n is a number from 0 to 4 and preferably equal to 0, 1, or 2,
$R_1$ represents a hydrogen atom or an alkyl, cycloalkyl, aryl or aralkyl group,
$R_2$, which may be identical or different, represent an alkyl, alkoxy or hydroxyl group, a halogen atom or a perhaloalkyl group;
by reaction of the compound of formula (I) with an oxidizing agent, in the presence of a titano-silicalite zeolite prepared by crystallization, preceded by a maturation step.

In the context of the invention, the term "alkyl" means a linear or branched $C_1$-$C_{15}$, preferably $C_1$-$C_{10}$ and even more preferentially $C_1$-$C_4$ hydrocarbon-based chain. Examples of preferred alkyl groups are especially methyl, ethyl, propyl, isopropyl, butyl, isobutyl and t-butyl.

The term "alkoxy" means a group alkyl-O— in which the term "alkyl" has the meaning given above. Preferred examples of alkoxy groups are methoxy or ethoxy groups.

The term "cycloalkyl" means a $C_3$-$C_8$ monocyclic, cyclic hydrocarbon-based group, preferably a cyclopentyl or cyclohexyl group or a $C_4$-$C_{18}$ polycyclic (bicyclic or tricyclic) group, especially adamantyl or norbornyl.

The term "aryl" means a monocyclic or polycyclic aromatic, preferably $C_6$-$C_{20}$ monocyclic or bicyclic group, preferably phenyl or naphthyl. When the group is polycyclic, i.e. when it comprises more than one cyclic nucleus, the cyclic nuclei may be fused in pairs or attached in pairs via σ bonds. Examples of ($C_6$-$C_{18}$)aryl groups are especially phenyl and naphthyl.

The term "aralkyl" means a linear or branched hydrocarbon-based group bearing a $C_7$-$C_{12}$ monocyclic aromatic ring, preferably benzyl: the aliphatic chain comprising 1 or 2 carbon atoms.

The term "perhaloalkyl group" means an alkyl group comprising from 1 to 10 carbon atoms and from 3 to 21 halogen atoms, preferably fluorine, and more particularly the trifluoromethyl group.

In formula (I), the term "halogen atom" preferably defines fluorine, chlorine and bromine.

The substrates to which the process of the invention applies are especially phenol; aliphatic phenol ethers; monoalkylphenols, dialkylphenols, trialkylphenols with $C_1$-$C_4$ alkyl groups; alkoxyphenols with $C_1$-$C_4$ alkoxy groups.

Among the substrates of formula (I) that may be used in the process of the invention, mention may be made in a nonlimiting manner of phenol; aliphatic phenol ethers such as anisole or phenetole; alkylphenols such as o-cresol, p-cresol, m-cresol, 4-tert-butylphenol (or para-tert-butylphenol); alkoxyphenols such as 2-methoxyphenol (guaiacol), 4-methoxyphenol or 2-ethoxyphenol (guetol).

Preferably, in the compound of formula (I), $R_1$ is a hydrogen atom, a methyl group or an ethyl group, and more preferably R1 is hydrogen. Even more preferably, n=0 in the compound of formula (I). Very advantageously, in the compound of formula (I), n=0 and $R_1$ is a hydrogen atom, a methyl group or an ethyl group. In a particularly preferred manner, the compound of formula (I) is phenol or anisole.

In another embodiment and advantageously, in the compound of formula (I), $R_1$ represents H, $R_2$ represents a tert-butyl and n=1, $R_2$ preferably being in the para position.

The hydroxylation process according to the invention makes it possible especially, Starting with phenol, to prepare hydroquinone and pyrocatechol with a PC/HQ mole ratio of less than 1.4, preferably less than 1.2, more preferably less than 1, preferably strictly less than 0.8 and more preferably strictly less than 0.7. Advantageously, the PC/HQ mole ratio is at least equal to 0.05.

Preferably, the oxidizing agent is hydrogen peroxide ($H_2O_2$). Preferably, the oxidizing agent is used in a mole ratio relative to the compound of formula (I) of from 0.005 to 0.60, preferably from 0.05 to 0.50 and even more preferably from 0.15 to 0.35. The hydrogen peroxide titer is typically from 10% to 70% and usually from 20% to 30%.

Preferably, the hydroxylation reaction is performed in the presence of a solvent, chosen especially from protic solvents and aprotic solvents, or a mixture of these solvents. The process may especially be performed in water, in a erotic solvent, in an aprotic solvent or in a water/protic solvent or water/aprotic solvent mixture. The protic solvent may be chosen from water, alcohols, especially methanol, ethanol, propanol, isopropanol or tert-butanol, and acids, especially acetic acid. The hydroxylation reaction is particularly preferably performed in water. The aprotic solvent may be acetone and any other ketone, nitriles such as acetonitrile, or esters such as methyl acetate, ethyl acetate, propyl acetate or butyl acetate.

Preferably, the solvent is used in a mole proportion of from 0.05 to 50 and preferably from 0.2 to 20, relative to compound (I).

According to one variant, as specified above, the water may be mixed with other solvents in water/solvent mole proportions of from 1/0.01 to 1/20 and preferably from 1/0.1 to 1/2.

In a particular embodiment, the process according to the invention is a process for the hydroxylation of phenol leading to the formation of pyrocatechol and hydroquinone. In a particularly advantageous manner, the process of the invention makes it possible to obtain hydroquinone and pyrocatechol in a PC/HQ mole ratio of less than 1.4, preferably less than 1.2, more preferably less than 1, even more preferably strictly less than 0.8 and more preferably strictly less than 0.7.

In another particular embodiment, the process according to the invention is a process for the hydroxylation of anisole.

In another particular embodiment, the process according to the invention is a process for the hydroxylation of para-tert-butylphenol.

The process of the invention may especially be performed at a temperature of from 50° C. to 120° C. and preferably from 70° C. to 100° C. The process of the invention may especially be performed for a period of from 5 minutes to several days, for example from 5 minutes to 100 hours.

The process according to the invention is advantageously performed in a reactor functioning in batch mode, in semi-batch mode or in continuous mode. Various types of reactor may be used for performing the process according to the invention. Advantageously, the process according to the invention is performed in a stirred reactor or a cascade of stirred reactors or alternatively in a piston-flow reactor, for example a tubular reactor placed horizontally, vertically or inclined.

The process according to the invention is preferably performed with a mass ratio of zeolite relative to the compound of formula (I) of from 0.001 to 0.30, preferably from 0.01 to 0.10 and even more preferably from 0.01 to 0.06.

Preferably, the matured titano-silicalite zeolite used for performing the hydroxylation process according to the invention is a zeolite TS-1 or TS-2, respectively, from the MFI family or from the MEL family. Such zeolites are described in the prior art, but are modified according to the invention by the introduction of a maturation step before crystallization to be used for performing the hydroxylation process according to the invention.

The present invention thus relates to a matured titano-silicalite zeolite, preferably matured TS-1 or TS-2, preferably TS-1, characterized by an apparent mean particle size of from 10 to 300 nm, preferably from 20 to 150 nm and more preferably from 35 to 75 nm. The mean apparent size of the crystallites was calculated, according to the Scherrer formula, from the mid-height width of x-ray diffraction lines. It was chosen to work with the line (101) (2θ=7.9°) (FIG. 1). The structural study of the various materials is performed using an X PERT Pro diffractometer. The diffractograms are recorded over a 2θ angular range from 5° to 90° at 200 seconds per 0.02° step. The size of the crystallites was also determined by means of an Ultra 55 Zeiss field effect scanning electron microscope (SEM/FEG) equipped with an InLens detector (FIG. 2) and a Jeol 2010F transmission electron microscope equipped with a field emission cannon functioning at 200 kV (FIG. 3). The size distribution of the crystallites was also determined by dynamic light scattering (DLS). The measurements were taken at 20° C.

using a Vasco DL135 granulometer from the company Cordouan Technologies. The size distribution of the crystallites was calculated from the autocorrelation function using the Padé-Laplace algorithm (FIG. 4). The measurements were applied to synthetic solutions (i.e. to the solutions obtained after maturation, after crystallization and before calcination of the materials) diluted from 10 to 400 times in demineralized water and/or treated with ultrasound for 1 to 10 minutes, but also to solutions obtained after dispersion of 50 to 100 mg of calcined catalyst in 10 g of demineralized water, and treated with ultrasound for 15 minutes.

Preferably, this zeolite is also characterized by an infrared absorption band at 550 $cm^{-1}$ and an infrared absorption band at 960 $cm^{-1}$ (FIG. 5). The infrared absorption bands at 420 $cm^{-1}$, 800 $cm^{-1}$, 1070 $cm^{-1}$ and 1220 $cm^{-1}$, conventionally obtained for any material based on $SiO_2$, are also observed. The ratio between the area of the band at 960 $cm^{-1}$ ($A_{960}$) and the area of the band at 550 $cm^{-1}$ ($A_{550}$) ranges between 0 and 1 and preferably between 0.4 and 0.7. The analyses were performed with a Jasco 4200 Fourier transform infrared spectrometer (FT/IR), in attenuated total reflection (ATR), between 400 and 4000 $cm^{-1}$.

Preferably, this zeolite is also characterized by a UV absorption band of between 210 and 240 nm (FIG. 6). The presence of titanium oxide (UV absorption band at about 330-360 nm) may also be demonstrated by this characterization technique. The analyses were performed with a Perkin-Elmer Lambda 950 spectrophotometer for wavelengths of between 190 and 500 nm.

The matured zeolite according to the invention used in the hydroxylation process according to the invention may be advantageously obtained via a manufacturing process comprising a maturation step.

Advantageously, this maturation step makes it possible to obtain a zeolite with an outer surface area (measured from the slope of the nitrogen adsorption curve represented according to the t-plot method) of from 60 $m^2/g$ to 300 $m^2/g$ and preferably from 60 to 150 $m^2/g$ and/or an inter-grain distance (measured according to the Barrett-Joyner-Halenda method=BJH method) of from 5 to 50 nm and preferably from 10 to 30 nm. Advantageously, the specific surface area of this zeolite (measured according to the Brunauer-Emmett-Teller method=BET method) is between 350 and 600 $m^2/g$ and preferably between 400 and 500 $m^2/g$. The micropore size is particularly between 0.40 and 0.50 nm and preferably between 0.44 and 0.46 nm (measured by the Horvath-Kawazoe method=HK method). The measurement of the amount of nitrogen that is able to be adsorbed onto the surface of a porous solid, as a function of the relative pressure $P/P_0$, makes it possible to determine the specific surface area, the volume and the diameter of the pores. The adsorption and desorption of nitrogen are performed in liquid nitrogen (at −196° C.) using a Belsorp Max machine. The sample is pretreated under a secondary vacuum at 250° C. for 16 hours. The mass of analyzed sample is about 50-100 mg. Nitrogen adsorption and desorption isotherms for a TS-1 are reported as in the example in FIG. 7. The nitrogen adsorption takes place first in the micropores. Consequently, analysis of the first part of the curve ($P/P_0$<0.02) makes it possible to determine the volume and size of the micropores (BET method and HK method). Next, once the micropores have been filled, adsorption takes place on the outside of the particles. Exploitation of the second part of the curve (0.02<$P/P_0$<0.85) gives access to the outer surface area of the material (measured from the t-plot method). Finally, for relative pressures of greater than 0.85, we observe hysteresis due to capillary condensation in the mesopores of the material. These mesopores are inter-grain pores, derived from clogging together the particles. Analysis of the final part of the curve ($P/P_0$>0.85) makes it possible to determine the volume and size of the mesopores (equivalent to the inter-grain distance) (BJH method).

Preferably, the zeolite has a mole ratio Ti/(Ti+Si) of from 0.0001 to 0.10 and preferably from 0.0001 to 0.05, for example from 0.005 to 0.04.

The present invention also relates to a process for preparing a titano-silicalite zeolite, comprising the following steps:
a) preparation of a zeolite precursor from at least one source of silicon, at least one source of titanium, at least one mineralizing agent and at least one structuring agent;
b) maturation of the precursor;
c) crystallization of the matured precursor, and optionally
d) calcination of the matured and crystallized precursor, especially to obtain the zeolite according to the invention.

Step a) of preparing the precursor may be performed according to any method known to those skilled in the art.

In a particular embodiment, step a) is performed according to A. J. H. P. Van Der Pol et al. (Appl. Catal. A General 1992 92 93-111), and especially comprises the following steps:
i. mixing the source of titanium and the source of silicon;
ii. adding to the solution obtained in i), dropwise, under cold conditions, preferably at 0° C., an aqueous solution of structuring agent and of mineralizing agent;
iii. heating the solution obtained in ii) to a temperature of from 60 to 100° C., preferably 80° C.;
iv. adding demineralized water.

Preferably, the mixture according to step (i) is stirred for 30 minutes to 2 hours, preferably for 1 hour, at a temperature of from 20 to 50° C. and preferably from 25 to 40° C.

Preferably, step (ii) is performed under an inert atmosphere, for example under argon.

In another particular embodiment, step a) is performed according to A. Thangaraj et al. (J. Catal. 1991, 130, 1-8), and especially comprises the following steps:
1) mixing a source of silicon and an aqueous solution of structuring agent and of mineralizing agent;
2) mixing a source of titanium and an alcohol, especially isopropanol;
3) adding the solution from step 2) to the solution from step 1) dropwise at low temperature, preferably 0° C.;
4) heating;
5) adding demineralized water.

Preferably, the mixing according to step 1) is performed at room temperature (20-25° C.) for 0.5 to 5 hours and preferably for 2 to 4 hours before step 3).

Preferably, the temperature of step 4) is from 60 to 100° C., for example 80° C.

In another particular embodiment, step a) is performed according to Serrano et al. (Micro. Mater. 1995, 4, 273-282), and especially comprises the following steps:
A) hydrolysis of a source of silicon with an acidified aqueous solution, preferably an aqueous HCl solution;
B) dissolution of a source of titanium in an alcohol, especially isopropanol;
C) addition of solution B) to solution A);
D) addition of an aqueous solution of structuring agent and of mineralizing agent;
E) drying and obtaining a solid material;

F) impregnation of the material obtained in step E) with an aqueous solution of structuring agent and of mineralizing agent dropwise, and homogenization.

At the end of step D), the material sets to a solid.

Step E) is performed at a temperature of from 60 to 130° C., for example at 100° C.; for 6 hours to 5 days, for example for 3 days.

The source of titanium and the source of silicon may be any compound known to those skilled in the art that may serve for the preparation of titano-silicalite zeolite (for example those described by Perego et al. (Applied Catalysis A: General, 2001, 221, 63-72)). Preferably, the sources of titanium and silicon are chosen from titanium or silicon oxides, titanium or silicon alkoxides and titanium or silicon halides. Preferably, the source of titanium is a titanium alkoxide, for example tetraethoxytitanium (TEOT) or tetrabutoxytitanium (TBOT). Preferably, the source of silicon is a silicon alkoxide, for example tetraethyl orthosilicate (TEOS).

According to the invention, the term "structuring agent" means a structure-directing agent which will allow the formation of the zeolite. The term "mineralizing agent" means any chemical species whose role is to catalyze the hydrolysis and polycondensation of the sources of titanium and silicon. The same species may act as structuring agent and as mineralizing agent. The various structuring agents that may be used, alone or as mixtures, for preparing TS-1 are chosen from tetrapropylammonium (TPA$^+$), tetraethylammonium (TEA$^+$), tetrapropylphosphonium (TPP$^+$), tetraethylphosphonium (TEP$^+$) and hexapropyl-1,6-hexanediammonium (di-TPA$^+$), the mineralizing agent then possibly being the counterion chosen from HO$^-$, F$^-$ and amine. The various structuring agents that may be used, alone or as mixtures, for preparing TS-2 are chosen from tetrabutylammonium (TBA$^+$) and 3,5-dimethyl-N,N-diethylpiperidinium (DMDEP$^+$), the mineralizing agent then possibly being the counterion chosen from HO$^-$, F$^-$ and amine.

Preferably, in the process of the invention, tetrapropylammonium hydroxide (TPAOH) acts as structuring agent and mineralizing agent (TPA$^+$ structuring agent and HO$^-$ mineralizing agent). The aqueous solution of structuring agent is typically an aqueous solution containing between 20% and 40% by weight of structuring agent.

Advantageously, the mole ratios of structuring agent/Si and mineralizing agent/Si, and especially the mole ratio TPAOH/Si, are from 0.09 to 0.55 and preferably from 0.17 to 0.45.

Advantageously, the H$_2$O/Si mole ratio is between 4 and 80 and preferably between 10 and 30.

In a particularly advantageous manner, step b) of maturation of the titano-silicalite zeolite corresponds to a step of thermal heating, before crystallization, with or without stirring, at a temperature of from 20 to 120° C., preferably at a temperature of from 70 to 100° C. and more preferentially 80° C. or 90° C. Preferably, the maturation step b) is performed for between 30 minutes and 9 months and preferably between 1 hour and 15 days. In a particular embodiment, the maturation step b) corresponds to a step of thermal heating, before crystallization, at a temperature of from 20 to 120° C. and preferably from 20 to 110° C., for 30 minutes to 9 months. Preferably, the maturation step is performed between 70 and 100° C. for between 1 hour and 15 days and preferentially at 80° C. for between 10 and 35 hours or alternatively at 90° C. for between 2 and 20 hours. The maturation time will preferentially be shorter for a higher temperature.

In another embodiment, the step of maturation of the titano-silicalite zeolite corresponds to a step of microwave heating, before crystallization, with or without stirring, at a temperature of from 40 to 120° C., for 1 to 180 minutes. At a temperature equivalent to a thermal heating, microwave heating will make it possible to shorten the maturation time. At a time equivalent to a thermal heating, microwave heating will make it possible to reduce the maturation temperature.

The crystallization step c) may be performed, with or without stirring, at the autogenous pressure of the system or under a pressure of an inert gas, for example nitrogen, for example at a pressure of from 10 to 120 bar and preferably from 20 to 120 bar.

In another embodiment, the crystallization step c) may be performed with or without stirring, by microwave heating at a temperature of from 140 to 200° C., for example 175° C., for a time of less than 8 hours and particularly preferably less than 3 hours, for example from 1 to 60 minutes.

The process for preparing the titano-silicalite zeolite may also comprise a step of washing the crystalline material of step c). This step may be performed via any method known to those skilled in the art and especially by washing with deionized water. This step may especially be performed by dispersing the material obtained in step c) in a deionized water, and this washing step may be repeated several times and preferably until the pH of the solution after washing is less than 9.

The process for preparing the zeolite may also comprise a step of recovering the washed material. This step may be performed via any method known to those skilled in the art and especially by centrifugation, especially by centrifugation at low temperature. The material thus obtained is then dried by any method known to those skilled in the art, especially by atomization or simple drying at a temperature of from 70 to 110° C., for 10 to 48 hours.

The process for preparing the zeolite may also comprise a final step of calcination, This step may be performed via any method known to those skilled in the art, especially by heating at a temperature of from 350 to 750° C., for example at 550° C., for 2 to 24 hours.

Preferably, the maturation step b) makes it possible to reduce the duration of the crystallization step a) by thermal heating which should usually be more than 1 day at 175° C., without modifying the catalytic performance of the zeolite. Thus, in a particularly advantageous manner, the crystallization step is performed, with or without stirring, from 140 to 200° C., for example at 175° C. for a time of less than 1 day, preferably less than 12 hours and particularly preferably less than 8 hours, for example from 3 to 6 hours.

The present invention also relates to a titano-silicalite zeolite that may be obtained via the process for preparing the same.

In general, the sizes of the particles obtained after maturation, after crystallization and before calcination are equivalent, or even identical, to those obtained after maturation, after crystallization and after calcination.

The present invention will now be described with the aid of nonlimiting illustrative examples.

In the examples, all the percentages are given on a weight basis, unless otherwise indicated, the temperature is expressed in degrees Celsius, unless otherwise indicated, and the pressure is atmospheric pressure, unless otherwise indicated.

In FIG. 1, I represents the scattered intensity and θ represents half of the angle between the incident beam and the scattered beam.

In FIG. 5, R represents the reflectance and σ represents the wavenumber.

In FIG. 6, F(R∞) represents the Kubelka-Munk function for an infinite thickness of powder and λ represents the wavelength.

Figure 1:
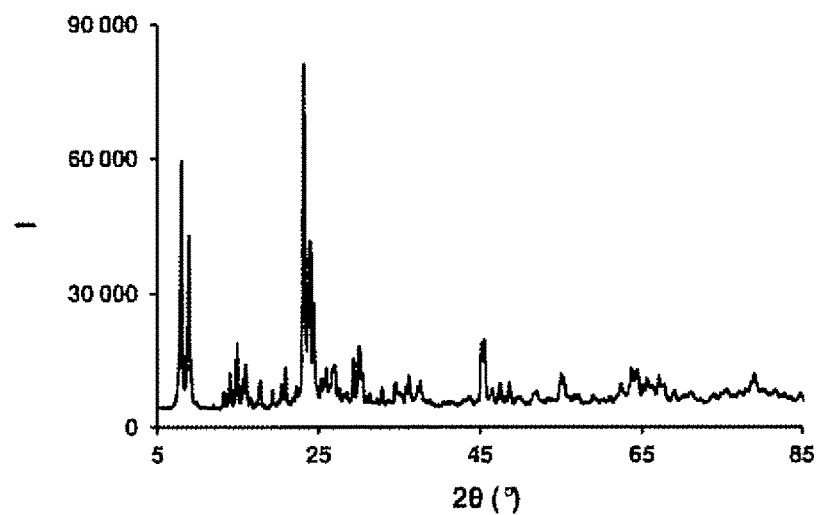
FIG. 1 shows the X-ray diffractogram of a titano-silicalite zeolite of TS-1 type which has undergone a step of maturation at 80° C. for 14 hours, and which has then been crystallized for 5 days at 175° C.
Figure 2:
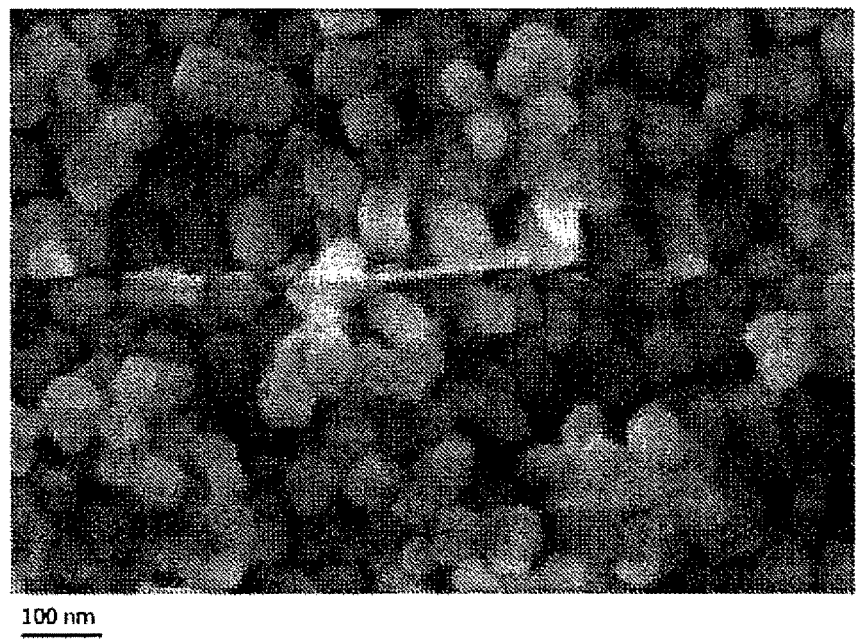
FIG. 2 is an SEM image of a titano-silicalite zeolite of TS-1 type which has undergone a step of maturation at 80° C. for 14 hours, and which has then been crystallized for 5 days at 175° C.
Figure 3:
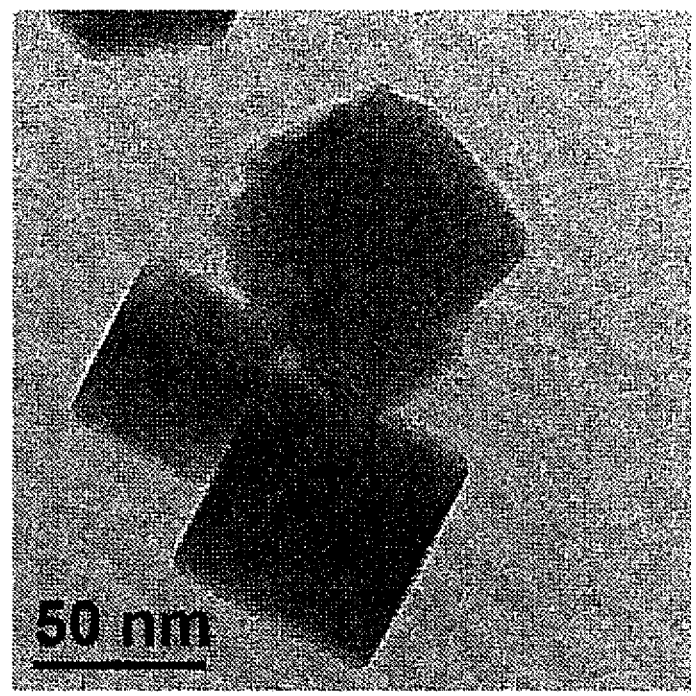
FIG. 3 is a TEM image of a titano-silicalite zeolite of TS-1 type which has undergone a step of maturation at 80° C. for 23 hours, and which has then been crystallized for 5 days at 175° C.
Figure 4:
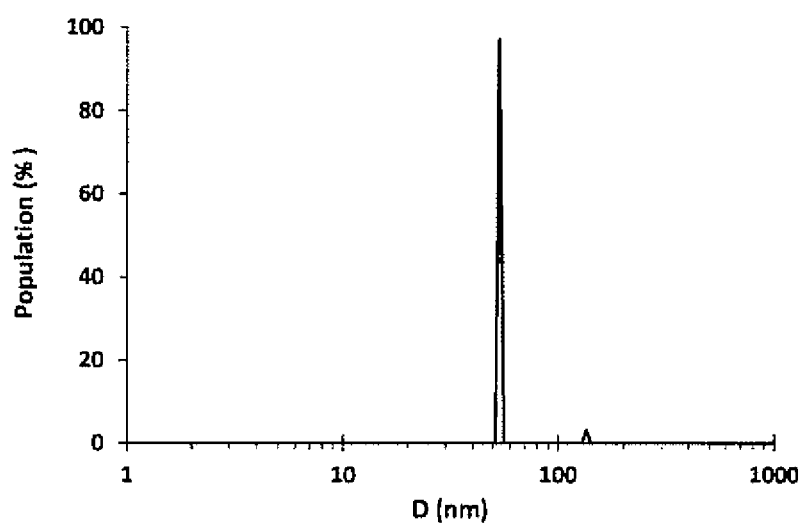
FIG. 4 shows the population (percentage of the number of particles) as a function of the diameter D of the particles of a titano-silicalite zeolite of TS-1 type which has undergone a step of maturation at 80° C. for 23 hours, and which has then been crystallized for 5 days at 175° C.
Figure 5:
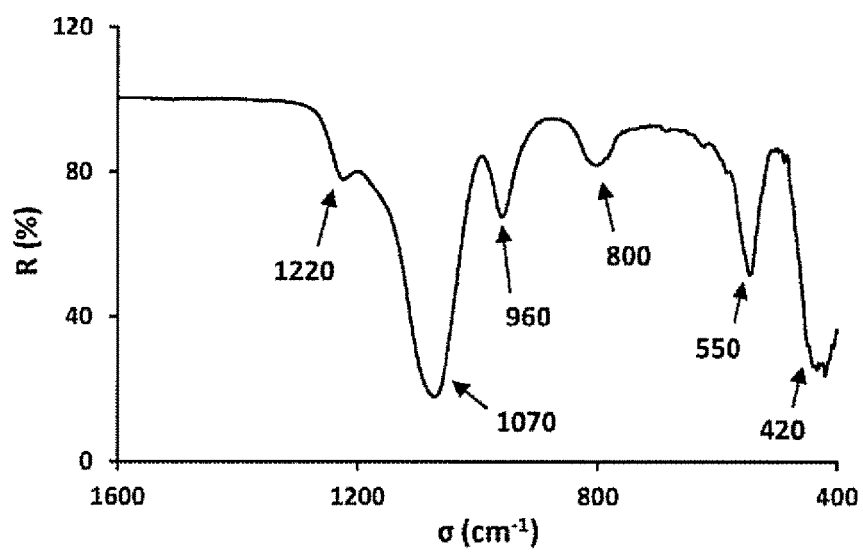
FIG. 5 shows the IR spectrum of a titano-silicalite zeolite of TS-1 type which has undergone a step of maturation at 80° C. for 14 hours, and which has then been crystallized for 5 days at 175° C.
Figure 6:
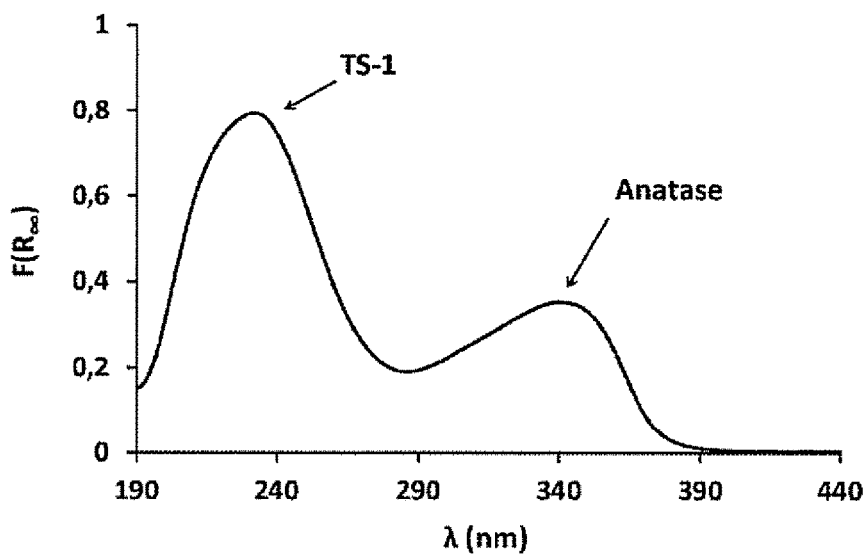
FIG. 6 shows the UV spectrum of a titano-silicalite zeolite of TS-1 type which has undergone a step of maturation at 80° C. for 14 hours, and which has then been crystallized for 5 days at 175° C.
Figure 7:
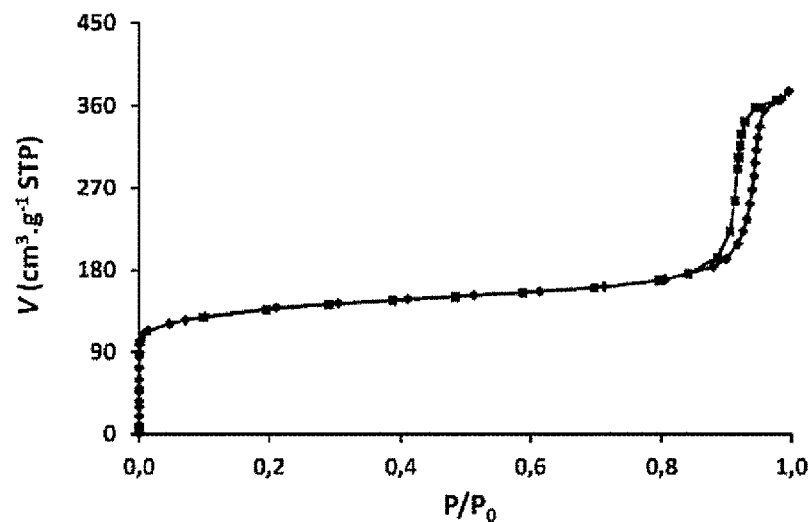

FIG. 7 shows the nitrogen adsorption and desorption isotherms for a titano-silicalite zeolite of TS-1 type which has undergone a step of maturation at 80° C. for 14 hours, and which has then been crystallized for 5 days at 175° C. In FIG. 7, V represents the specific adsorbed volume in gas equivalent under standard temperature and pressure conditions (STP) and $P/P_0$ represents the relative pressure of gas relative to atmospheric pressure.

Figure 8:
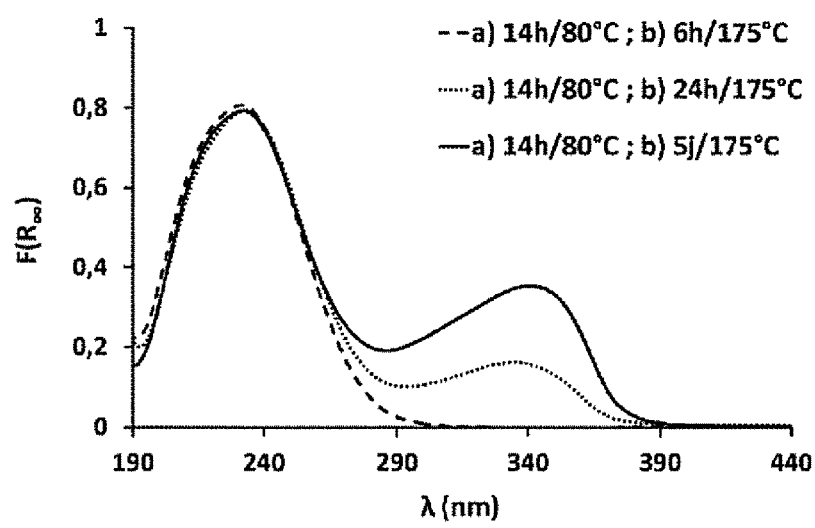

FIG. 8 shows the UV spectra of various titano-silicalite zeolites of TS-1 type matured at 80° C. for 14 hours, and then crystallized at 175° C., for 6 hours, 24 hours or 5 days. In FIG. 8, F(R∞) represents the Kubelka-Munk function for an infinite thickness of powder and λ represents the wavelength.

EXAMPLES

Process A for Preparing a titano-silicalite Zeolite According to the Invention
Preparation of the Precursor 377 mmol of $Si(OEt)_4$ (TEOS) (Sigma Aldrich ≥99.0%) and 8 mmol of $Ti(OEt)_4$ (TEOT) (Alfa Aesar 99+%) are added to a polypropylene flask flushed with a stream of argon. This first solution is then stirred for 1 hour at 35° C. Next, a second solution containing 132 mmol of $(C_3H_7)_4NOH$ (TPAOH) at 20% by weight in water is prepared by dilution with demineralized water of the 25% commercial solution (Acros). The addition of the TPAOH solution takes place at 0° C., dropwise. The reaction mixture is then heated at 80° C. for about 3 hours. Finally, 37 g of demineralized water are added so that the volume of the precursor solution is equal to ⅔ of the volume of the autoclave in which the titano-silicalite zeolite is then crystallized. The molar composition of the resulting clear solution is: $SiO_2/TiO_2/TPAOH/H_2O=1/0.02/0.35/21$.
Maturation of the Precursor
The precursor obtained is placed in a 250 mL autoclave and is then heated without stirring at a given temperature of 80° C. or 90° C., under the autogenous pressure, for a given time of from 4.5 to 48 hours.
Crystallization
The matured precursor is crystallized, without stirring, at 175° C., under the autogenous pressure, for 6 hours to 5 days.
Washing, Drying, Calcination
The material obtained after the crystallization step is recovered by centrifugation for 30 to 45 minutes, at 9° C. and 12 000 rpm, and is then washed, i.e. dispersed in about 150 to 200 mL of demineralized water and left stirring for about 1 hour. The washing operation is repeated a sufficient number of times (in general three times) such that the pH of the final washing water is less than 9. Between each wash, the solid is recovered by centrifugation for 30 to 45 minutes, at 9° C. and 12 000 rpm. Next, the product is dried at 80° C. for about 16 hours and is then calcined at 550° C. in air for 3 hours.

This process A describes the preparation of a titano-silicalite-1 (TS-1) zeolite. The production of a titano-silicalite-2 (TS-2) zeolite is possible by replacing, during the preparation of the precursor, the TPAOH with TBAOH or any other structuring agent allowing the synthesis of TS-2.

Process B for Preparing a titano-silicalite Zeolite
Preparation of the Precursor
377 mmol of TEOS and 132 mmol of TPAOH at 20% by weight in water are added to a polypropylene flask flushed with a stream of argon. This first solution is then stirred for 3 hours at room temperature. A second solution is then prepared by diluting 8 mmol of $Ti(OC_4H_9)_4$ (TROT) (Acros 99%) in 218 mmol of isopropanol (Acros 99.5%). The addition of this second solution takes place dropwise at 0° C., with continued flushing with argon. The various alcohols present are then removed by heating the reaction mixture at 80° C. for about 3 hours. Finally, 37 g of demineralized water are added so that the volume of the precursor solution is equal to ⅔ of the volume of the autoclave in which the titano-silicalite zeolite is then crystallized. The molar composition of the resulting clear solution is: $SiO_2/TiO_2/TPAOH/H_2O=1/0.02/0.35/21$.
Maturation of the Precursor
The precursor obtained is placed in a 250 mL autoclave and is then heated at 80° C. without stirring, under the autogenous pressure, for a given time of 14 hours.
Crystallization
The matured precursor is crystallized, without stirring, at 175° C., under the autogenous pressure, for 5 days.
Washing, Drying, Calcination
The material obtained after the crystallization step is recovered by centrifugation for 30 to 45 minutes, at 9° C. and 12 000 rpm, and is then washed, i.e. dispersed in about 150 to 200 mL of demineralized water and left stirring for about 1 hour. The washing operation is repeated a sufficient number of times (in general three times) such that the pH of the final washing water is less than 9. Between each wash, the solid is recovered by centrifugation for 30 to 45 minutes, at 9° C. and 12 000 rpm. Next, the product is dried at 80° C. for about 16 hours and is then calcined at 550° C. in air for 3 hours.

Process C for Preparing a titano-silicalite Zeolite
Preparation of the Precursor
211 mmol of TEOS are first hydrolysed with 35.2 mL of an aqueous solution of HCl at 237 mmol/L, with stirring, at room temperature for 2 hours. 4.3 mmol of TBOT predissolved in 1.61 mol of isopropanol are added to this solution. The mixture obtained is then left stirring for 20 minutes. Next, 14 mmol of TPAOH at 25% by weight in water are added dropwise. A few seconds after the addition of the TPAOH, the $SiO_2$—$TiO_2$ cogel sets to a solid. This solid is then dried at 100° C. for 3 days. 16.7 g of dry cogel are then recovered. This cogel is ground and then impregnated with 60 mmol of TPAOH at 20% by weight in water. This impregnation is performed by adding the aqueous solution of TPAOH dropwise to the cogel placed in a polypropylene beaker. The mixture is homogenized using a spatula. Finally, a relatively fluid paste is obtained, the molar composition of which is $SiO_2/TiO_2/TPAOH/H_2O=1/0.02/0.35/13$.

Maturation of the Precursor

The precursor obtained is placed in a 250 mL autoclave and is then heated at 80° C. without stirring, under the autogenous pressure, for a given time of 14 hours.

Crystallization

The matured precursor is crystallized, without stirring, at 175° C., under the autogenous pressure, for 5 days.

Washing, Drying, Calcination

The material obtained after the crystallization step is recovered by centrifugation for 30 to 45 minutes, at 9° C. and 12 000 rpm, and is then washed, i.e. dispersed in about 150 to 200 mL of demineralized water and left stirring for about 1 hour. The washing operation is repeated a sufficient number of times (in general three times) such that the pH of the final washing water is less than 9. Between each wash, the solid is recovered by centrifugation for 30 to 45 minutes, at 9° C. and 12 000 rpm. Next, the product is dried at 80° C. for about 16 hours and is then calcined at 550° C. in air for 3 hours.

Process D for Preparing a titano-silicalite Zeolite According to the Invention

Preparation of the Precursor 377 mmol of TEOS and 132 mmol of TPAOH at 20% by weight in water are added to a polypropylene flask flushed with a stream of argon. This first solution is then stirred for 3 hours at room temperature. A second solution is then prepared by diluting 8 mmol of $Ti(OC_4H_9)_4$ (TBOT) (Acros 99%) in 218 mmol of isopropanol (Acros 99.5%). The addition of this second solution takes place dropwise at 0° C., with continued flushing with argon. The various alcohols present are then removed by heating the reaction mixture at 80° C. for about 3 hours. Finally, 37 g of demineralized water are added so that the volume of the precursor solution is equal to ⅔ of the volume of the autoclave in which the titano-silicalite zeolite is then crystallized. The molar composition of the resulting clear solution is: $SiO_2/TiO_2/TPAOH/H_2O=1/0.02/0.35/21$.

Maturation of the Precursor

The precursor obtained is placed in a 250 mL autoclave and is then heated at 80° C. and 30 bar, without stirring, for a given time of 14 hours. The pressure is adjusted by means of an inert gas such as nitrogen.

Crystallization

The matured precursor is crystallized, without stirring, at 175° C. and 60 bar, for 5 days. The pressure is adjusted by means of an inert gas such as nitrogen.

Washing, Drying, Calcination

The material obtained after the crystallization step is recovered by centrifugation for 30 to 45 minutes, at 9° C. and 12 000 rpm, and is then washed, i.e. dispersed in about 150 to 200 mL of demineralized water and left stirring for about 1 hour. The washing operation is repeated a sufficient number of times (in general three times) such that the pH of the final washing water is less than 9. Between each wash, the solid is recovered by centrifugation for 30 to 45 minutes, at 9° C. and 12 000 rpm. Next, the product is dried at 80° C. for about 16 hours and is then calcined at 550° C. in air for 3 hours.

Phenol Hydroxylation Reaction

The hydroxylation of phenol is performed in a one-liter semi-batch stirred reactor (500 rpm), to which are first added 200 g of phenol, 60 g of solvent such as water, acetone or methanol and 6 g of catalyst (TS-1 or TS-2). The reactor is equipped with a jacket in which circulates a heat-exchange fluid heated to 85° C. to obtain a temperature of 80° C. in the reaction medium. The start of the reaction corresponds to the start of introduction of the 69.5 g of hydrogen peroxide at 26% by weight in water. This solution is added dropwise over 2 hours. After the end of addition of the aqueous hydrogen peroxide solution, two or three samples of 5 to 10 g of the reaction medium are collected. These samples make it possible both to determine the remaining amount of hydrogen peroxide by potentiometric assay, and also to quantify, by liquid-phase chromatographic analysis, the pyrocatechol (PC) and hydroquinone (HQ). Under these operating conditions, the phenol/$H_2O_2$/$H_2O$ mole ratio is 1/0.25/2.9 and the phenol/TS-1 mass ratio is 1/0.03.

Assay of the Aqueous Hydrogen Peroxide Solution and of the Phenol Conversion Products The aqueous hydrogen peroxide solution is assayed by oxidation of iodide ions and back-assay of the formed iodine with sodium thiosulfate. The potentiometric titration station used for this analysis is a Titrelab® 865 from the company Radiometer Analytical.

Pyrocatechol and hydroquinone are analyzed by liquid-phase chromatography (Agilent 1200 series).

In the examples that follow, the following abbreviations have the meanings as follows:

The degree of conversion ($DC(H_2O_2)$) of hydrogen peroxide corresponds to the ratio between the number of moles of hydrogen peroxide converted and the number of moles of hydrogen peroxide introduced.

The diphenol reaction yield ($RY(HQ+PC)/H_2O_2$) corresponds to the ratio between the number of moles of diphenols formed (pyrocatechol+hydroquinone) and the number of moles of hydrogen peroxide introduced.

The pyrocatechol reaction yield ($RY(PC)/H_2O_2$) corresponds to the ratio between the number of moles of pyrocatechol formed and the number of moles of hydrogen peroxide introduced.

The hydroquinone reaction yield ($RY(HQ)/H_2O_2$) corresponds to the ratio between the number of moles of hydroquinone formed and the number of moles of hydrogen peroxide introduced.

The diphenol selectivity ($CY(HQ+PC)/H_2O_2$) corresponds to the ratio between the number of moles of diphenols formed (pyrocatechol+hydroquinone) and the number of moles of hydrogen peroxide converted.

EXAMPLE 1

Effect of the Maturation Step on the Catalytic Performance of TS-1 in the Phenol Hydroxylation Reaction The phenol hydroxylation reaction described above was performed with zeolites obtained according to process C (examples 1.1 and 1.2), according to process A (example 1.3), according to process D (example 1.4) and according to process B (example 1.5) in which the maturation step is performed at 80° C. for 14 hours, the crystallization step at 175° C. for 5 days, and the calcination step at 550° C. for 3 hours. Samples were collected from the reaction medium 15 and 60 minutes after the end of the addition of $H_2O_2$. The results are presented in table 1.

Comparative reactions were performed with zeolites obtained according to process C (example 1.6), process A (example 1.7) and process D (example 1.8), but which did not undergo the maturation step. These zeolites only underwent the step of crystallization at 175° C. for 5 days and the step of calcination at 550° C. for 3 hours. Samples were collected from the reaction medium 15 and 60 minutes after the end of the addition of $H_2O_2$. The results are presented in table 2.

TABLE 1

| Sample collection | Examples according to the invention | | | | | | | | | |
|---|---|---|---|---|---|---|---|---|---|---|
| ($T_0$ = 2 h = | 1.1 | | 1.2 | | 1.3 | | 1.4 | | 1.5 | |
| addition time of $H_2O_2$) | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min |
| DC($H_2O_2$) (%) | 89 | 99 | 93 | 99 | 84 | 98 | 93 | 99 | 85 | 98 |
| RY(HQ)/$H_2O_2$ (%) | 49 | 53 | 46 | 46 | 43 | 46 | 49 | 49 | 40 | 49 |
| RY(PC)/$H_2O_2$ (%) | 30 | 32 | 29 | 28 | 27 | 29 | 29 | 31 | 29 | 30 |
| RY(HQ + PC)/$H_2O_2$ (%) | 79 | 85 | 75 | 74 | 70 | 75 | 78 | 80 | 70 | 78 |
| CY(HQ + PC)/$H_2O_2$ (%) | 89 | 86 | 81 | 75 | 83 | 76 | 83 | 80 | 82 | 79 |
| PC/HQ mole ratio | 0.62 | 0.61 | 0.63 | 0.62 | 0.64 | 0.63 | 0.59 | 0.63 | 0.73 | 0.61 |

TABLE 2

| Sample collection | Comparative examples | | | | | |
|---|---|---|---|---|---|---|
| ($T_0$ = 2 h = | 1.6 | | 1.7 | | 1.8 | |
| addition time of $H_2O_2$) | $T_0$ + 15 min | $T_0$ + 60 min | $T_0$ + 15 min | $T_0$ + 60 min | $T_0$ + 15 min | $T_0$ + 60 min |
| DC($H_2O_2$) (%) | 67 | 81 | 65 | 80 | 74 | 89 |
| RY(HQ)/$H_2O_2$ (%) | 26 | 31 | 24 | 28 | 32 | 37 |
| RY(PC)/$H_2O_2$ (%) | 20 | 24 | 21 | 23 | 23 | 26 |
| RY(HQ + PC)/$H_2O_2$ (%) | 46 | 54 | 45 | 52 | 55 | 63 |
| CY(HQ + PC)/$H_2O_2$ (%) | 69 | 67 | 69 | 65 | 74 | 71 |
| PC/HQ mole ratio | 0.78 | 0.77 | 0.89 | 0.83 | 0.71 | 0.70 |

The results show that the catalytic performance of the materials crystallized after the maturation step are markedly better than those of the materials crystallized without maturation. Specifically, from a kinetic point of view, 15 minutes after the end of addition of the aqueous hydrogen peroxide solution ($T_0$+15 min), an $H_2O_2$ conversion of 84% for a matured TS-1 prepared according to protocol A (example 1.3) is observed, whereas it is only 65% for the material synthesized according to the same protocol but without the maturation step (example 1.7). Furthermore, for an equivalent conversion of hydrogen peroxide (about 80%), this same material has a selectivity toward PC+HQ relative to hydrogen peroxide of 83% (example 1.3), whereas it is only 69% for its non-matured homolog (example 1.7). The same observations may be made with all of the TS-1 products synthesized according to the other protocols. Furthermore, it is observed, independently of the synthetic protocol, that a PC/HQ mole ratio close to 0.60 is obtained for the TS-1 products matured for 14 hours at 80° C.

EXAMPLE 2

Effect of the Maturation Step on the Structure of the TS-1

Zeolites were prepared according to process A (example 2.1), process D (example 2.2), process C (example 2.3) and process B (example 2.4) with a maturation step at 80° C. for 4.5 to 48 hours or without a maturation step. All the zeolites prepared underwent a step of crystallization at 175° C. for 5 days and a step of calcination at 550° C. for 3 hours.

The size of the crystallites was determined by X-ray diffraction (XRD) and transmission electron microscopy (TEM) after the maturation, crystallization and calcination steps. The size of the crystallites was also determined by dynamic light scattering (DLS) using synthetic aqueous solutions (i.e. solutions obtained after maturation, after crystallization and before calcination of the materials) diluted from 10 to 400 times in demineralized water and/or treated with ultrasound for 1 to 10 minutes, but also using solutions obtained after dispersion of 50 to 100 mg of matured, crystallized and calcined catalyst in 10 g of demineralized water, and treated with ultrasound for 15 minutes. The outer surface area and the inter-grain distance were determined by adsorption/desorption of nitrogen. The results are presented in table 3.

TABLE 3

| | | | DLS | | | | Nitrogen adsorption/desorption | |
|---|---|---|---|---|---|---|---|---|
| | | XRD Apparent mean size of the crystallites (line 101) (nm) | Size after maturation and crystallization and before calcination (nm) | Size after maturation, crystallization and calcination (nm) | Population (% of the number of crystallites) | TEM Crystallite size (nm) | $S_{outer}$ ($m^2$/g) [tplot] | $D_{inter-grain}$ (nm) [BJH] |
| Examples | Maturation | | | | | | | |
| 2.1 | None | 80 | — | — | — | 90-160 | 39 | 50 ± 20 |
| | 4.5 h/ 80° C. | 67 | 71 | 71 | 94 | 50-110 | 63 | 22 ± 7 |
| | 14 h/ 80° C. | 55 | — | 59 | 97 | 30-90 | 79 | 19 ± 5 |
| | 23 h/ 80° C. | 56 | 56 | 54 | 97 | 30-90 | 83 | 16 ± 6 |

TABLE 3-continued

| Examples | Maturation | XRD Apparent mean size of the crystallites (line 101) (nm) | DLS Size after maturation and crystallization and before calcination (nm) | DLS Size after maturation, crystallization and calcination (nm) | Population (% of the number of crystallites) | TEM Crystallite size (nm) | Nitrogen adsorption/desorption $S_{outer}$ (m²/g) [tplot] | Nitrogen adsorption/desorption $D_{inter-grain}$ (nm) [BJH] |
|---|---|---|---|---|---|---|---|---|
| | 48 h/ 80° C. | 55 | 51 | 51 | 98 | 40-90 | 82 | 21 ± 7 |
| 2.2 | None | 95 | — | — | — | — | 33 | 40 ± 15 |
| | 14 h/ 80° C. | 50 | — | — | — | — | 72 | 19 ± 5 |
| 2.3 | None | 110 | — | — | — | — | 22 | 60 ± 20 |
| | 14 h/ 80° C. | 68 | — | — | — | — | 60 | 30 ± 10 |
| 2.4 | 14 h/ 80° C. | 55 | — | — | — | — | 79 | 19 ± 6 |

The main characteristic of the materials matured at 80° C. is that the apparent mean size of the particles is about 1.5 to 2 times smaller than that of the non-matured materials (size determined after OLS analysis, observation by TEM and calculated after XRD analysis from the mid-height width of the line (101)). Furthermore, irrespective of the synthetic protocol, it is observed that TS-1 particles of 50 to 70 nm are obtained if the zeolite has undergone a maturation step, irrespective of the maturation time at 80° C. Since the particles are smaller after maturation, the space between the grains ($D_{inter-grain}$ determined via the BJH method) is consequently smaller. Furthermore, the zeolites matured for 4.5 to 48 hours at 80° C. have an outer surface area about twice as large as that of the non-matured materials. From the DLS, irrespective of the synthetic protocol and the maturation time at 80° C., the size of the crystallites obtained after the maturation and crystallization steps and before the calcination step is similar, or even identical, to the size of the crystallites obtained after the maturation, crystallization and calcination steps.

EXAMPLE 3

Effect of the Maturation Time and Temperature on the Catalytic Performance of TS-1 in the Phenol Hydroxylation Reaction The hydroxylation reaction presented above was performed with different zeolites prepared according to protocol A which have undergone a maturation step at 80° C. for 4.5 hours (example 3.2), for 14 hours (example 3.3), for 23 hours (example 3.4) and for 48 hours (example 3.5) and at 90° C. for 14 hours (example 3.6) and for 23 hours (example 3.7).

A comparative example (example 3.1) of hydroxylation of phenol was also performed with a zeolite obtained via process A, but which was not subjected to the maturation step.

All the zeolites prepared underwent a step of crystallization at 175° C. for 5 days and a step of calcination at 550° C. for 3 hours.

Samples were collected from the reaction medium 15 and 60 minutes after the end of the addition of $H_2O_2$. The results are presented in table 4.

TABLE 4

| Sample collection | Examples 3.1 | | 3.2 | | 3.3 | | 3.4 | | 3.5 | | 3.6 | | 3.7 | |
|---|---|---|---|---|---|---|---|---|---|---|---|---|---|---|
| | Maturation | | | | | | | | | | | | | |
| ($T_0$ = 2 h = addition | None | | 4.5 h/ 80° C. | | 14 h/ 80° C. | | 23 h/ 80° C. | | 48 h/ 80° C. | | 14 h/ 90° C. | | 23 h/ 90° C. | |
| time of $H_2O_2$) | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min | $T_0$ + 15 min | $T_0$ + 60 min |
| DC($H_2O_2$) (%) | 65 | 80 | 80 | 94 | 84 | 98 | 93 | 99 | 65 | 82 | 78 | 95 | 83 | 98 |
| RY(HQ)/ $H_2O_2$ (%) | 24 | 28 | 32 | 40 | 43 | 46 | 47 | 49 | 28 | 34 | 36 | 41 | 36 | 37 |
| RY(PC)/ $H_2O_2$ (%) | 21 | 23 | 23 | 28 | 27 | 29 | 29 | 30 | 20 | 24 | 24 | 27 | 24 | 24 |
| RY(HQ + PC)/ $H_2O_2$ (%) | 45 | 52 | 55 | 68 | 70 | 75 | 77 | 78 | 48 | 58 | 60 | 68 | 59 | 61 |
| CY(HQ + PC)/ $H_2O_2$ (%) | 69 | 65 | 69 | 72 | 83 | 76 | 83 | 79 | 74 | 71 | 77 | 72 | 71 | 63 |
| PC/HQ mole ratio | 0.89 | 0.83 | 0.69 | 0.69 | 0.64 | 0.63 | 0.62 | 0.60 | 0.71 | 0.69 | 0.68 | 0.65 | 0.66 | 0.65 |

It is noted that it is possible to vary the selectivity toward hydroquinone and pyrocatechol relative to hydrogen peroxide (CY(HQ+PC)/$H_2O_2$) which ranges between 60% and 85% by modifying the maturation temperature of between 80 and 90° C. and the maturation time of between 4.5 and 48 hours. On the other hand, irrespective of the matured catalysts, the PC/HQ mole ratios are similar or even identical and strictly less than 0.70.

EXAMPLE 4

Effect of the Crystallization Time on the Catalytic Performance of Matured TS-1 in the Phenol Hydroxylation Reaction The hydroxylation reaction presented above was performed with different zeolites prepared according to protocol A which have undergone a step of maturation at 80° C. for 14 hours and a step of crystallization at 175° C. for 6 hours (example 4.1), for 24 hours (example 4.2) and for 5 days (example 4.3). All the zeolites were calcined at 550° C. for 3 hours.

Samples were collected from the reaction medium 15 and 60 minutes after the end of the addition of $H_2O_2$. The results are presented in table 5.

TABLE 5

| | Examples | | | | | |
|---|---|---|---|---|---|---|
| | 4.1 | | 4.2 | | 4.3 | |
| | Crystallization | | | | | |
| Sample collection | 6 h/175° C. | | 24 h/175° C. | | 5 days/175° C. | |
| ($T_0$ = 2 h = addition time of $H_2O_2$) | $T_0$ + 15 min | $T_0$ + 60 min | $T_0$ + 15 min | $T_0$ + 60 min | $T_0$ + 15 min | $T_0$ + 60 min |
| DC($H_2O_2$) (%) | 84 | 98 | 95 | 99 | 84 | 98 |
| RY(HQ)/$H_2O_2$ (%) | 43 | 46 | 44 | 48 | 43 | 46 |
| RY(PC)/$H_2O_2$ (%) | 27 | 28 | 28 | 29 | 27 | 29 |
| RY(HQ + PC)/$H_2O_2$ (%) | 70 | 74 | 72 | 77 | 70 | 75 |
| CY(HQ + PC)/$H_2O_2$ (%) | 84 | 75 | 76 | 78 | 83 | 76 |
| PC/HQ mole ratio | 0.64 | 0.61 | 0.62 | 0.61 | 0.64 | 0.63 |

The results show that after maturation for 14 hours at 80° C., the crystallization time at 175° C. may be lowered to 6 hours without modifying the catalytic performance of the TS-1. Specifically, at virtually total conversion of the hydrogen peroxide, the CY(HQ+PC)/$H_2O_2$ values are very similar and, respectively, 75%, 78% and 76% for crystallizations times at 175° C. of 6 hours, 24 hours and 5 days. Finally, irrespective of the crystallization time at 175° C., the PC/HQ mole ratio is 0.60.

EXAMPLE 5

Effect of the Crystallization Time on the Characteristics of the TS-1

Different zeolites prepared according to protocol A underwent a step of maturation at 80° C. for 14 hours and a step of crystallization at 175° C. for 6 hours (example 5.1), for 24 hours (example 5.2) and for 5 days (example 5.3). All the zeolites were calcined at 550° C. for 3 hours.

The size of the crystallites was determined by XRD and DLS. The results are presented in table 6.

TABLE 6

| | | | XRD Apparent | DLS | |
|---|---|---|---|---|---|
| Examples | Crystallization | Ti/(Ti + Si) molar (±0.001) | mean size of the crystallites (line 101) (nm) | Size (nm) | Population (% of the number of crystallites) |
| 5.1 | 6 h/175° C. | 0.013 | 49 | — | — |
| 5.2 | 24 h/175° C. | 0.016 | 53 | 54 | 93 |
| 5.3 | 5 days/175° C. | 0.020 | 55 | 59 | 97 |

The results show that the size of the crystallites, of about 50 nm, does not depend on the crystallization time at 175° C. for materials matured beforehand for 14 hours at 80° C. On the other hand, it is observed that the titanium content of the material increases as the crystallization time increases. The mole ratio Ti/(Ti+Si) is, respectively, 0.013, 0.016 and 0.020 for crystallization times at 175° C. of 6 hours, 24 hours and 5 days. The increase in titanium content of 0.013 to 0.016 and 0.020 corresponds to the increasingly large formation of anatase, as evidenced in FIG. 8.

EXAMPLE 6

Effect of the Nature of the Solvent in the Phenol Hydroxylation Reaction in the Presence of a Catalyst of the titano-silicalite Zeolite Type The hydroxylation reaction presented above was performed with different solvents or a mixture of solvents such as water (example 6.1), water/acetone (example 6.2) and water/methanol (example 6.3).

The zeolite used for the phenol hydroxylation reaction was prepared according to protocol A and was first subjected to a step of maturation at 80° C. for 23 hours, and then a step of crystallization at 175° C. for 5 days, and finally a step of calcination at 550° C. for 3 hours.

Samples were collected from the reaction medium 15, 60 or 120 minutes after the end of the addition of $H_2O_2$. The results are presented in the table below.

| Sample collection ($T_0 = 2$ h = addition time of $H_2O_2$) | Examples | | | | | | | |
|---|---|---|---|---|---|---|---|---|
| | 6.1 | | 6.2 | | | 6.3 | | |
| | Solvent | | | | | | | |
| | Water | | Water/acetone | | | Water/methanol | | |
| | $T_0 +$ 15 min | $T_0 +$ 60 min | $T_0 +$ 15 min | $T_0 +$ 60 min | $T_0 +$ 120 min | $T_0 +$ 15 min | $T_0 +$ 60 min | $T_0 +$ 120 min |
| DC($H_2O_2$) (%) | 93 | 99 | 67 | 84 | 97 | 70 | 90 | 98 |
| RY(HQ)/$H_2O_2$ (%) | 47 | 49 | 27 | 32 | 35 | 32 | 36 | 37 |
| RY(PC)/$H_2O_2$ (%) | 29 | 30 | 26 | 30 | 33 | 22 | 25 | 25 |
| RY(HQ + PC)/$H_2O_2$ (%) | 77 | 78 | 52 | 62 | 68 | 54 | 60 | 62 |
| CY(HQ + PC)/$H_2O_2$ (%) | 83 | 79 | 79 | 74 | 70 | 77 | 67 | 63 |
| PC/HQ mole ratio | 0.62 | 0.60 | 0.96 | 0.95 | 0.94 | 0.69 | 0.69 | 0.69 |

The results show that the best solvent for the hydroxylation of phenol is water used alone. Specifically, from a kinetic point of view, 60 minutes after the end of addition of the hydrogen peroxide ($T_0$+60 min), a total conversion of the hydrogen peroxide is observed for the hydroxylation of phenol in water, whereas it is only 84% and 90% for the hydroxylation of phenol, respectively, in water/acetone and water/methanol. Furthermore, for an equivalent conversion of hydrogen peroxide (about 100%), the hydroxylation of phenol in water leads to a selectivity toward PC+HQ relative to the hydrogen peroxide of 79%, which is higher than that obtained for the hydroxylation of phenol in the water/acetone and water/methanol mixtures, which are, respectively, 70% and 63%. Finally, the lower PC/HQ ratio was obtained for the hydroxylation of phenol in water (PC/HQ=0.60). This is, respectively, 0.94 and 0.69 for the hydroxylation of phenol in the water/acetone and water/methanol solvent mixtures.

The invention claimed is:

1. A matured TS-1 or TS-2 titano-silicalite zeolite having:
   an apparent mean particle size of from 35 to 75 nm,
   an outer surface area of from 60 m²/g to 150 m²/g, and
   an inter-grain distance of from 10 to 30 nm.
2. The matured TS-1 or TS-2 titano-silicalite zeolite according to claim 1 further having a specific surface area of between 350 and 600 m²/g.
3. The matured TS-1 or TS-2 titano-silicalite zeolite according to claim 1 further having a specific surface area of between 400 and 500 m²/g.
4. The matured TS-1 or TS-2 titano-silicalite zeolite according to claim 1 further having micropores of between 0.40 and 0.50 nm.
5. The matured TS-1 or TS-2 titano-silicalite zeolite according to claim 1 further having micropores of between 0.44 and 0.46 nm.
6. The matured TS-1 or TS-2 titano-silicalite zeolite according to claim 1 further having a mole ratio Ti/(Ti+Si) of from 0.0001 to 0.10.
7. A TS-1 or TS-2 titano-silicalite zeolite that may be obtained by the process comprising the following steps:
   a) preparation of a zeolite precursor from at least one source of silicon, at least one source of titanium, at least one mineralizing agent and at least one structuring agent;
   b) maturation of the zeolite precursor for obtaining a matured precursor;
   c) crystallization of the matured precursor for obtaining a matured crystalline precursor, and optionally
   d) calcination of the matured crystalline precursor, wherein said maturation step consists in a step of thermal heating of said zeolite precursor, before crystallization, at a temperature of from 70 to 100° C.

* * * * *